(12) United States Patent
Wu (10) Patent No.: US 8,426,371 B2
(45) Date of Patent: Apr. 23, 2013

(54) **BIOLOGICALLY ACTIVE EXTRACT FROM *DENDROBIUM* PLANT, USE THEREOF AND PROCESS FOR PREPARING THE SAME**

(75) Inventor: Rong-Tsun Wu, Taipei (TW)

(73) Assignee: National Yang-Ming University, Taipei (TW)

( * ) Notice: Subject to any disclaimer, the term of this patent is extended or adjusted under 35 U.S.C. 154(b) by 0 days.

(21) Appl. No.: 12/715,117

(22) Filed: Mar. 1, 2010

(65) Prior Publication Data

US 2011/0003761 A1    Jan. 6, 2011

Related U.S. Application Data

(62) Division of application No. 11/824,247, filed on Jun. 29, 2007, now abandoned.

(51) Int. Cl.
*A61K 31/7048* (2006.01)
*A61P 27/02* (2006.01)

(52) U.S. Cl.
USPC .............................................. 514/27; 514/23

(58) Field of Classification Search .................... 514/23, 514/27
See application file for complete search history.

(56) References Cited

U.S. PATENT DOCUMENTS

| 7,101,577 B2 | 9/2006 | Wu | |
| 7,776,326 B2 * | 8/2010 | Milbrandt et al. | ........... 424/94.5 |
| 2009/0005324 A1 | 1/2009 | Wu | |

FOREIGN PATENT DOCUMENTS

| JP | 04059788 A | | 2/1992 |
| JP | 04059788 A | * | 2/1992 |

OTHER PUBLICATIONS

Chiou, G.C.Y. et al, J. Ocular Pharm. Therap., 2004, 20(2), 107-113.*
Free Online Medical Dictionary.com, 2007, pp. 1-2.*
Materska et al., "Antioxidant Activity of the Main Phenolic Compounds Isolated from Hot Pepper Fruit (*Capsicum annuum* L.)" J. Agric. Food Chem., 53:1750-1756 (2005).
Rao et al., "Phytochemical Investigation on Leaves of *Rhynchosia densiflora*", Indian J. Nat Prod., 14(1): 20-22 (1998).
Siewek et al., "Isomeric Di-C-glycosylflavones in Fig. (*Ficus carcia* L.)", Z. Naturforsch, 40c:8-12 (1985).
Xie et al., "Flavone C-Glycosides from *Viola yedoenisis* Makino", Chem Pharm. Bull. 51(10):1204-1207 (2003).
Sato et al. "Dose-Dependent of Sugar Cataracts in Galactose-fed Dogs by the Aldose Reductase Inhibitor M79175" Exp. Eye Res. 66:217-222 (1998).
Smith et al. "Systematic Evaluation of The Mouse Eye: Anatomy, Pathology and Biomethods" p. 320.
Friedman, Eli, "Aldose reductase inhibitors in the prevention of diabetic complications", UpToDate http://www.uptodate.com/contents/aldose-reductase-inhibitors-in-the-prevention-of-di . . . 2011.
Sorbinil Retinopathy Trial (SRT)—Sorbinil Retinopathy Trial (SRT)—Full Text View—ClinicalTrials.gov—http://clinicaltrials.gov/ct2/show/study/NCT00000159?term=aldose+reductase+inhibit . . . (2005).

* cited by examiner

*Primary Examiner* — Shaojia Anna Jiang
*Assistant Examiner* — Ganapathy Krishnan
(74) *Attorney, Agent, or Firm* — Porzio, Bromberg & Newman, P.C.

(57) ABSTRACT

A substance having the following formula is provided.

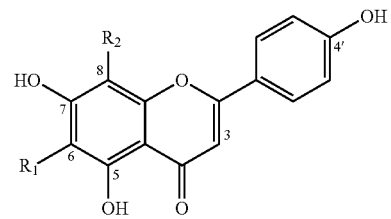

wherein $R_1$ and $R_2$ are selected from a group consisting of α-Arabinose, β-Arabinose and β-Xylose. The substance has an effect of accelerating a phagocytosis of RPE.

11 Claims, 11 Drawing Sheets

BIOLOGICALLY ACTIVE EXTRACT FROM *DENDROBIUM* PLANT, USE THEREOF AND PROCESS FOR PREPARING THE SAME

This application is a divisional of U.S. Ser. No. 11/824,247, filed on Jun. 29, 2007 now abandoned, the content of which is hereby incorporated by reference in its entirety.

FIELD OF THE INVENTION

This invention relates to a process for preparing a biologically active extract from a plant and the extract thereof, and especially to one process of using a water miscible organic solvent or a mixture thereof with water for obtaining an extract from the plant.

BACKGROUND OF THE INVENTION

As described in U.S. Pat. No. 7,101,577, it is known that the Dendrobium species is considered to be the most precious Chinese herb for treating ophthalmic defects. According to our previous research experience, it appears that the *Herba Dendrobii* (which, in tradition, is the generalized name for the Dendrobium plants having the curative effects) has the most biological effects. However, in recent years, it appears there is a trend of that the Dendrobium plants having the curative effects on their stems are generally named as *Caulis Dendrobii* and the Dendrobium plants having the curative effects on their whole plants are generally called as *Herba Dendrobii*.

Based on the descriptions in the mentioned application, it is known retinal pigment epithelium (RPE) is a monolayer cell at the surface layer of the retina, which is located between the Bruch's membrane and the photoreceptors. Since the RPE can effectively remove or transmit the toxic materials and the metabolite of the choroid coat and the retina, it performs a very important blood-retinal barrier. In addition, the RPE has many functions, such as receiving light, phagocytizing the outer segments separated from the rod cell and the cone cell because of light stimulation, catabolizing the phagosome, synthesizing the extracellular matrix and the melanin, detoxifying the medicine, providing the essential material for reproducing the outer segments of the photoreceptor, storing and transmitting the Vitamin A, synthesizing the rhodopsin, and forming the adherent force of the retina. The normal phagocytosis of the RPE plays a critical role in maintaining the health of the photoreceptors in the retina. Once the function of phagocytosis is reduced, it will result in the degeneration of the photoreceptors. Although the RPE will be dead or moved to someplace else with the increasing age, the aged RPE still owns the phagocytic ability. Further, the lost quantity of the rod cells are more than those of the cone cells, which causes the diseases and the vision degradation of the aged people. Therefore, maintaining the RPE function is quite important for the visional system.

In the immune system, the Nitric oxide (NO) plays a defensive role and is toxic to cells. In the blood vessel system, the NO is a so-called endothelium derived relaxing factor (EDRF). And, in the central nervous system, the NO acts as a neurotransmitter.

The NO is released from the process of transferring L-arginine into L-citrulline via a nitric oxide synthase (NOS). The NOS includes three kinds of isoforms, a neuronal NOS, an endothelial NOS and an immunologic NOS. The neuronal NOS and the endothelial NOS are constitutive forms, named as cNOS, whose activities are regulated by the calcium ion ($Ca^{++}$) and the calmodulin, and the concentration of the released NO is in the level of nano-molarity (nM). The immunologic NOS is an inducible form, named as iNOS, whose activity is not regulated by the $Ca^{++}$ and the calmodulin, and the concentration of the released NO is in the level of milli-molarity (mM). The genes of the cNOS and the iNOS are respectively located on different chromosomes.

In retina, the NOS has been found in the retinal neuron, RPE, amacrine cells, ganglion cells, and Müller cells. It appears that the NO plays an important role in the physiology and pathology, and is closely related to the functions of the eye.

It's found that the NO owns the ability of regulating the blood flow of the retina under a basal condition or an ischemia environment. Further, it's believed that the NO may own the ability of regulating the damage degrees of the blood vessels in the retina, in which the damage is caused by diabetes. In addition, when the retinal glial cells and the RPE are stimulated by the lipopolysaccharides (LPS), Interferon-γ (IFN-γ), and the tumor necrotic factor-α (TNF-α), the NOS will be largely expressed, which largely increase the production of the NO. In other words, under the conditions that the retina is inflamed or infected, the NO might play a role in the defense and protection mechanisms.

Till now, the position and the characteristics of the cNOS in the photoreceptor are still unclear. Some references disclose that the main body of the photoreceptor has the cNOS activities, and other references disclose that only the photoreceptor outer segments own the cNOS activities. The released NO can regulate the transmission of light, the transmitted message of the neutron synapse, and the blood flow of the retina under a physiological condition or an ischemia environment. The iNOS activity can also be found in some cells in the retina, such as the RPE and the Müller cells. In the culture of a bovine RPE, after being stimulated for 12 hours with the IFN-65, LPS, and TNF-α, a mass of NO will be released for at least 96 hours. The effects of the cytokines on the RPE iNOS activity are quite complex. In a bovine RPE, for instance, being stimulated by the LPS and the IFN-γ, or the TNF-α are necessary for releasing a mass of NO. The basic fibroblast growth factor (bFGF) inhibits the functions of NOS, but the transforming growth factor-β (TGF-β) slightly enhances the functions of the NOS. For a human RPE, it is necessary to be stimulated by the Interleukin-1β to release a mass of NO. However, the LPS is not the necessary factor to stimulate a human RPE. In addition, the TGF-β obviously inhibits the release of the NO in a human RPE.

When infected by bacteria, the expressions of iNOS may be beneficial because the released NO will kill the invaded microorganism. Contrarily, in some cases, when the released NO is exceeded, the released NO will result in the autoimmune diseases or the septic shock. In 1994, the first evidence for explaining the relationship between NO and the inflammation of the fundus oculi is proposed, and the reference also proposed that the uveitis resulted from the endotoxins can be blocked by the iNOS inhibitor. On the other hand, it appears that the acidic fibroblast growth factor (aFGF) and the bFGF can inhibit RPE from generating a mass of NO by treating the RPE with IFN-γ and LPS. Since it is the expression of the iNOS, but not the stabilities of the iNOS being mRNA, is inhibited, it's conjectured that the FGF will protect the RPE from being damaged by the endotoxins and the cytokines. Thus, it can be seen that the iNOS also plays a role in regulating the immunity of the retina.

The common retinal diseases include the proliferative diabetic retinopathy caused by the diabetes, the proliferative vitreoretinopathy, and the Aged-macular degeneration. However, the retinal diseases are the hardest diseases to cure in the ophthalmic defects. The hyperglycemia accelerates the glycation, which forms the advanced glycation end products (AGEs), and it is believed that the AGEs closely relates to the vascular complication or the neuronal complication. An unstable schiff base is formed via the nonenzymatic reaction between the aldehyde group or the ketone group of the reducing sugar and the primary amino acids of the protein. Then, an amadori product is formed from the schiff base via the amadori rearrangement. And, the advanced glycosylation end product (AGE) will be formed from the amadori product via the rearrangement process. It is known that the nonenzymatic glycosylation is not a reversible reaction and usually occurs at the protein having a long half-life. While the AGE formation results in cross-linking, the protein molecule would have a resistance to the protease. Therefore, the accumulation of the AGE would be an aging mark. With the increasing age, the AGE amounts in the pyramidal neurons of the brain, the Bruch's membrane and the collagen will increase gradually. The reactive rate of the nonenzymatic glycosylation is a primary reaction, and the reaction rate is dependent on the concentrations of the reducing sugar and the protein. Usually, a diabetic patient has a higher blood glucose concentration than normal people, so that the glycosylation situation will be increased. It is known that the diabetic patients have higher probabilities of having some diseases or symptoms for the normal people are all directly related to the AGE, in which the disease or symptoms include the atherosclerosis, the kidney impair, the vessel damage, the neuron disease, the retinopathy, and the apoplexy. The main reason for the aggregation of the erythrocyte, resulted from the diabetes, is that the tertiary structure of the albumin is changed after being glycosylated, so that the glycosylated albumin loses the functions of the anti-aggregation. Further, the reason for changing the permeability of the glomerulus is the glycosylation of the albumin but not the glycosylation of the glomerular basement membrane. In addition, the glycosylated protein has a better ability for penetrating the blood brain barrier.

The AGE can combine with some receptors on the cell surface or some proteins. The known receptors include the scavenger receptors type I, the scavenger receptors type II, the receptor for AGE (RAGE), OST-48 (AGE-R1), 80K-H phosphoprotein (AGE-R2), and the galectin-3 (AGE-R3). Besides, the RAGE can be found at the surfaces of the monocyte, the macrophage, the endothelial cell, and the glia cell. When the cell is activated by the AGE, the expressions of the extracellular matrix protein, the vascular adhesion molecules, and the growth factors will increase. Depending on the different cell types and the transmitted signals, some phenomena will occur accompanied with the above situation, such as the chemotaxis, the angiogenesis, the oxidative stress, the cell proliferation and the programmed cell death. It appears that the various cells in the human brain are able to express different RAGEs, which remove the AGE. When the remove ability is lost, the AGE will be accumulated outside the cell, which induces the inflammation reaction of the central nervous system. Furthermore, the AGE will induce the expressions of both the retinal vascular endothelial growth factor of the RPE and the platelet-derived growth factor-β (PDGF-β). The AGE plays an important role in the aging process, so that designing a pathological model by the glycosylated albumin for developing a new medicine is very important.

The most important growth factor in the liver is the hepatocyte growth factor/scatter factor (HGF/SF), which is formed by combining the 60 KDa heavy chain (α chain) with the 30 KDa light chain (β chain) through the disulfide bond. The newly formed HGF/SF is the preproHGF/SF, which needs to be modified by an enzyme for forming the heterodimeteric form before having a biological activity. The HGF is a multi-function growth factor, which not only has the ability for regulating the growth of the various cells, but also plays an important role in the tissue repair and the organ regeneration. The internal distribution of the HGF is very extensive, wherein the liver has the highest quantity of the HGF. Furthermore, the HGF can be found in the pancreas, the thymus, the blood, the small intestines, the placenta and so forth. In addition, the HGF/SF or the HGF/SF receptors are found in the eye secretions and the eye tissues, such as the tears, the lachrymal gland, and the cornea, so that it is conjectured that the HGF may play a role in the regulation of eyes. Besides, it's known that the RPE has both the HGF and the HGF receptor (c-Met). Since the tyrosine phosphorylation of the c-Met expresses all the time, the HGF may be a growth factor with the self-stimulation function for the RPE. Further, the HGF may be related to the development of the retina, the wound healing, and the newborn retinal vessels.

From the above, it is known that RPE plays an important role in retinal regulation mechanisms. Meanwhile, it has been proved that the Chinese herb, Dendrobium species, is able to enhance or inhibit some functions or regulation mechanisms in RPE. More specifically, the Dendrobium species can enhance the expressions of RPE phagocytosis, the NO formation of the RPE, the gene expressions of the RPE liver hepatocyte growth factor. The Dendrobium species can inhibit the gene expressions of the bFGF, the vascular endothelial growth factor (VEGF) and the TGF-β in the RPE under a normal condition and an ischemia environment. Consequently, the relevant researches about the enhancing factors of the RPE activities are important for improving the health of the body. In the preceding researches, it has known that the extract from *Herba Dendrobii* has an effect of accelerating a phagocytosis of RPE and increases the AGE degradation. In order to further control the effect of accelerating the phagocytosis of RPE, further understanding about the extract from *Herba Dendrobii* is desired.

SUMMARY OF THE INVENTION

In accordance with an aspect of the present invention, a composition having a substance with a structure of the following formula 1 is provided.

formula 1 wherein $R_1$ and $R_2$ are the same or different functional groups.

Preferably, the composition has an effect of accelerating a phagocytosis of RPE.

Preferably, the substance is one selected from the group consisting of apigenin 6,8-Di-C-α-L-arabinopyranoside, apigenin 6-C-β-D-Xylopyranosyl-8-C-α-L-arabinopyranoside, apigenin 6-C-α-L-Arabinopyranosyl-8-C-β-D-arabinopyranoside and the mixture thereof.

Preferably, the composition is physiologically active.

In accordance with another aspect of the present invention, a substance with a structure of the following formula 2 is provided.

formula 2 wherein $R_1$ and $R_2$ are selected from a group consisting of α-Ara, β-Ara and β-Xyl.

Preferably, the substance has an effect of accelerating a phagocytosis of RPE.

Preferably, R1 and R2 are the same or different and are selected from the group consisting of C-β-D-glucopyranosyl, C-β-D-galactopyranosyl, C-β-D-xylopyranosyl, C-β-D-arabinopyranosyl, C-α-L-arabinopyranosyl, C-α-L-rhamnopyranosyl and C-6-deoxy-xylo-hexos-4-ulosyl.

In accordance with a further aspect of the present invention, a composition having a carrier for carrying therewith the mentioned substance is provided.

Preferably, the composition is a pharmaceutical composition.

Preferably, the carrier is a physiologically acceptable carrier.

Preferably, the carrier is a pharmaceutical carrier.

The above objects and advantages of the present invention will become more readily apparent to those ordinarily skilled in the art after reviewing the following detailed descriptions and accompanying drawings, in which:

DETAILED DESCRIPTION OF THE PREFERRED EMBODIMENT

The present invention will now be described more specifically with reference to the following embodiments. It is to be noted that the following descriptions of preferred embodiments of this application are presented herein for purpose of illustration and description only; it is not intended to be exhaustive or to be limited to the precise form disclosed.

Preparation of the *Herba Dendrobii* extract and separation of the purified active content thereof.

Figure 1:
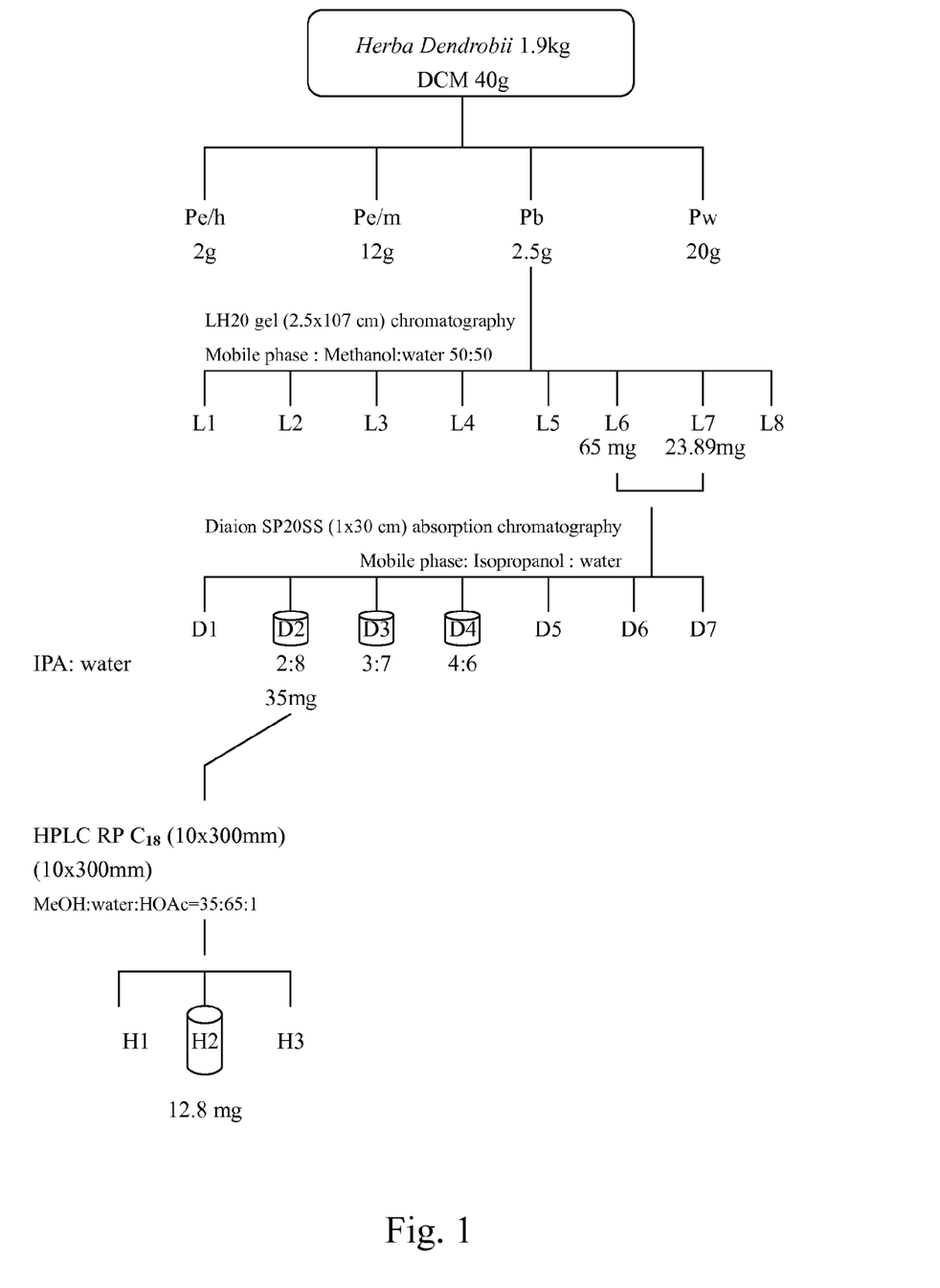
FIG. 1 is the flow chart of separating protocol for *Herba Dendrobii* extract according to a preferred embodiment of the present invention.

Please refer to FIG. 1. FIG. 1 is the flow chart of the separating protocol for *Herba Dendrobii* extract according to a preferred embodiment of the present invention. Three active components are separated from *Herba Dendrobii*. 1.9 kg *Herba Dendrobii* is extracted by methanol three times for obtaining the methanol extract of *Herba Dendrobii*. The methanol extract of *Herba Dendrobii* is then re-concentrated and completely dried for forming the DCM standard. The dry DCM standard is dissolved in 2 L EtOAc and then partitioned with 2 L water for obtaining an EtOAc layer and a first water layer. The water layer is extracted with 2 L EtOAc two more times. All the EtOAc layers are collected, re-concentrated and completely dried for obtaining the EtOAc extract. The dry EtOAc extract is respectively partitioned three times with 4 L hexane and 2 L methanol for obtaining a hexane layer and a methanol layer. After re-concentrated and dried, the dried hexane layer and methanol layer are named as DCMPe/h standard (Pe/h), and DCMPe/m standard (Pe/m) respectively. In addition, the first water layer is adjusted into 2 L volume by adding de-ionized water, and then is partitioned by adding 2 L butanol for obtaining a butanol layer and a second water layer. After re-concentrated and dried the dried butanol layer and the second water layer are named as DCMPb standard (Pb), and DCMPw standard (Pw) respectively. The Pb is extracted by LH20 gel chromatography with a molecule column (2.5× 107 cm, mobile phase <methanol:$H_2O$=50:50>). After the activity screening, the DCMPbL6,7 samples are obtained. Then, the samples DCMPbL6,7 are extracted by the Diaion SP-20 SS chromatography with y a absorption column (1×30 cm). When the mobile phase is isopropanol:$H_2O$=20:80, the eluate named as DCMPbL6,7D2 can be obtained. When the mobile phase is isopropanol:$H_2O$=30:70, the eluate named as DCMPbL6,7D3 can be obtained. When the mobile phase is isopropanol:$H_2O$=40:60, the eluate named as DCMPbL6, 7D4 can be obtained. Then, the DCMPbL6,7D2 is chromatographed by HPLC reverse C18 column (10×300 mm) with the mobile phase of methanol:$H_2O$:acetic acid=35:65:1, and the eluate named as DCMPbL6,7D2H2 is obtained.

Based on our preceding researches, it is known that DCMPbL6,7D2H2 has an effect of accelerating a phagocytosis of RPE and increases the AGE degradation. In order to further understand effect of accelerating a phagocytosis of RPE, some further operations are performed.

DCMPbL6,7D2H2 is chromatographed by HPLC reverse C18 column (10×300 mm) with the mobile phase of methanol:$H_2O$:acetic acid=40:60:1, and the eluate named as DCMPbL6,7D2H2H3 is obtained. Then, the DCMPbL6, 7D2H2H3 is further chromatographed by HPLC reverse C18 column (4.6×250 mm) with the mobile phase of methanol: H₂O=35:65, and the eluate named as DCMPbL6, 7D2H2H3H2 is obtained. Further, the DCMPbL6,7D2H2H3 is also chromatographed by HPLC reverse C18 column (4.6× 250 mm) with the mobile phase of methanol:H₂O=40:60, and the eluate named as DCMPbL6,7D2H2H3H3 is obtained. Moreover, the DCMPbL6,7D2H2H3 is also chromatographed by HPLC reverse C18 column (4.6×250 mm) with the mobile phase of methanol:H₂O=45:55, and the eluate named as DCMPbL6,7D2H2H3H4 is obtained.

Figure 2:
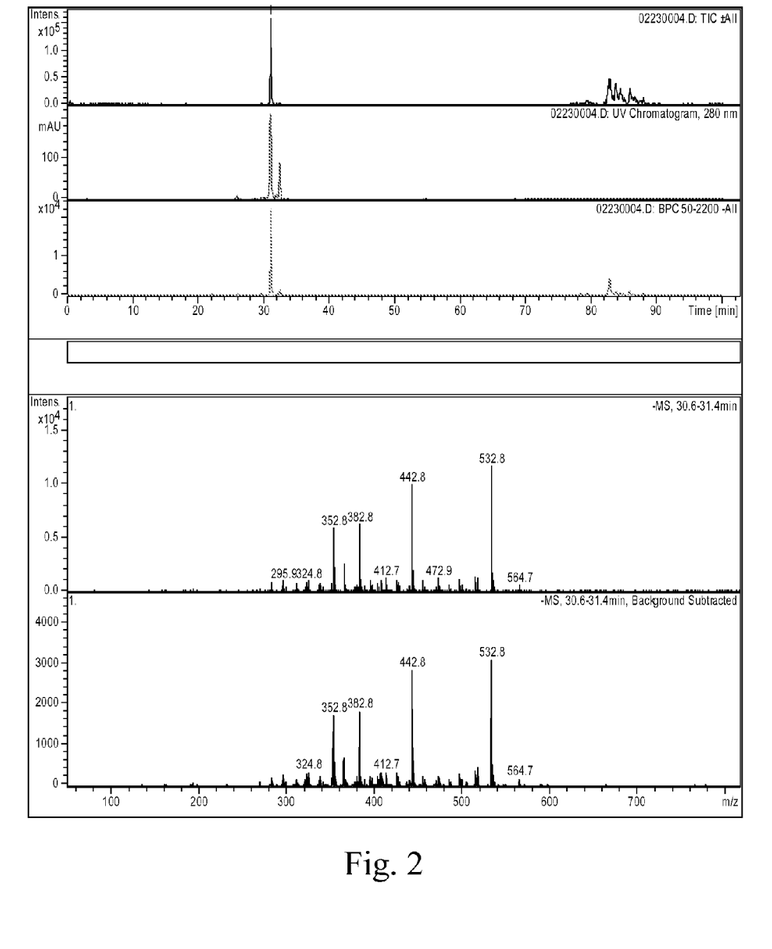
FIG. 2 is the LC-MS chromatography of DCMPbL6, 7D2H2H3.

Please refer to FIG. 2, which is the LC-MS chromatography of DCMPbL6,7D2H2H3. The analysis conditions for FIG. 2 are: column: Mightysil RP-C18 (4.6×250 mm), 5 μm; mobile phase: 0~80 min MeOH/H₂O=20/80 gradient to 100% MeOH, 80~100 min 100% MeOH; inject volume: 50 μl; inject weight: 5 μg; flow rate: 0.25 ml/min and UV: 337 nm.

Figure 3:
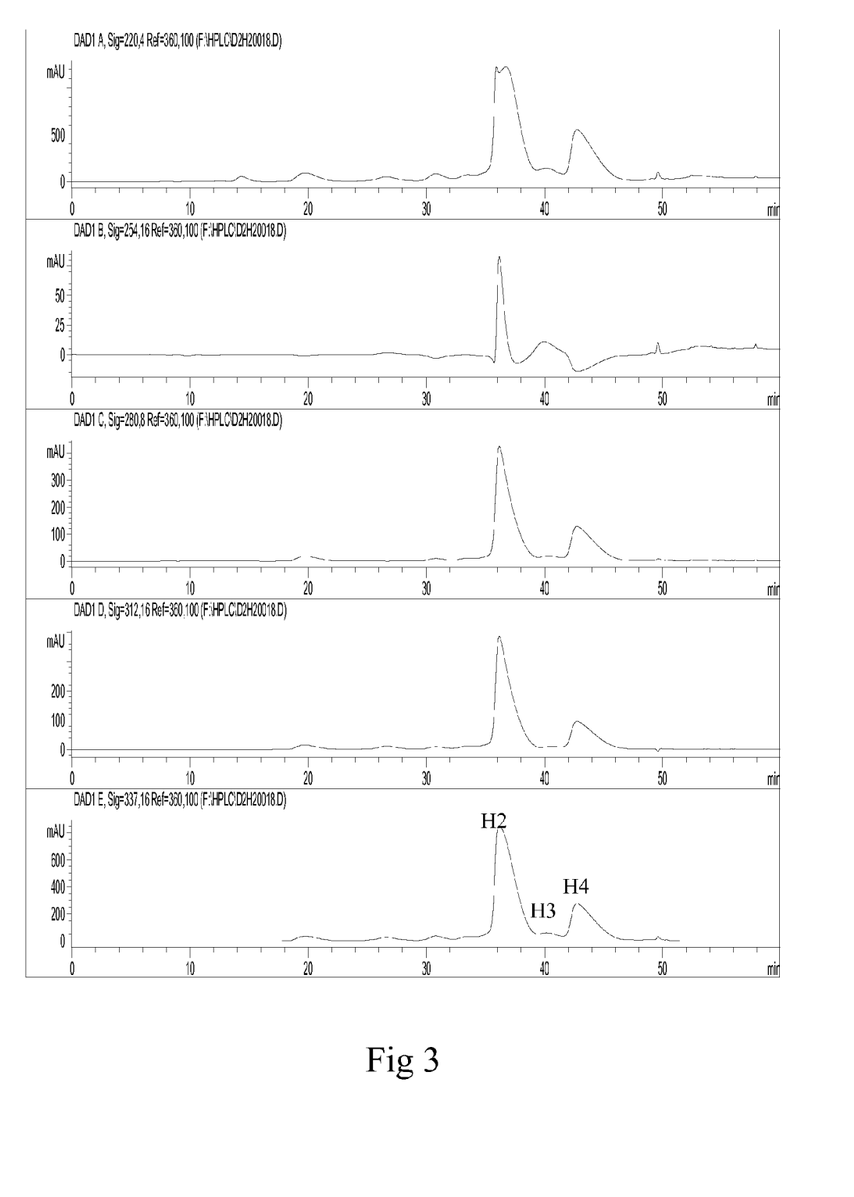
FIG. 3 is the HPLC chromatography of DCMPbL6, 7D2H2H3.

Please refer to FIG. 3, which is the HPLC chromatography of DCMPbL6,7D2H2H3. The analysis conditions for FIG. 3 are: column: Mightysil RP-C18 (4.6×250 mm), 5 μm; mobile phase: 0~40 min MeOH/H2O=35/65, 40~45 min MeOH/H₂O=35/65 gradient to 100% MeOH, 45~60 min 100% MeOH; inject volume: 250 μl; inject weight: 250 μg; flow rate: 0.8 ml/min and UV: 280, 312, 337 nm. H2 represents DCMPbL6,7D2H2H3H2, H3 represents DCMPbL6, 7D2H2H3H3, and H4 DCMPbL6,7D2H2H3H4.

Figure 4:
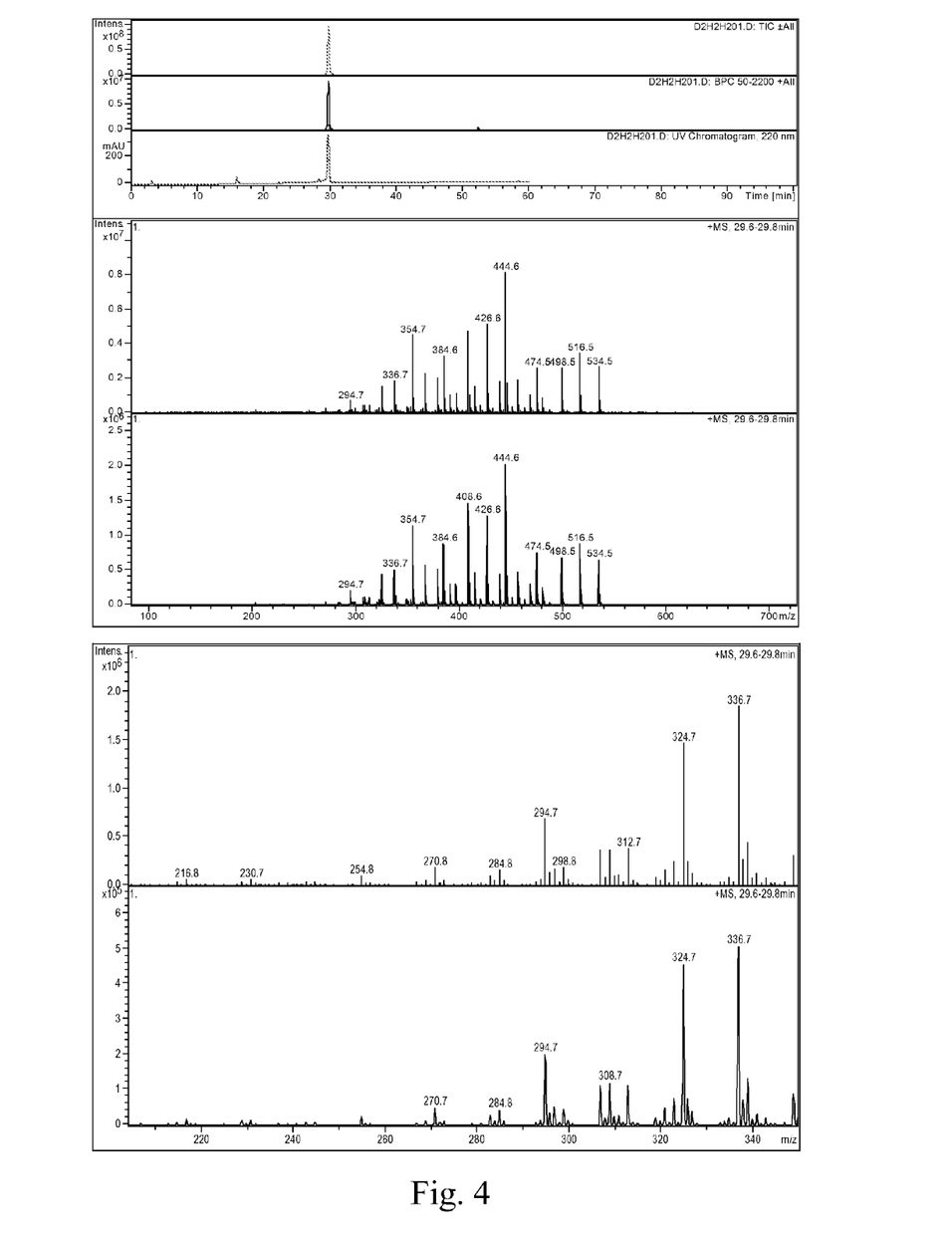
FIG. 4 is the LC-MS chromatography of DCMPbL6, 7D2H2H3H2.

Please refer to FIG. 4, which is the LC-MS chromatography of DCMPbL6,7D2H2H3H2. The analysis conditions for FIG. 4 are: column: Mightysil RP-C18 (4.6×250 mm), 5 μm; Mobile phase: 0~80 min MeOH/H₂O=20/80 gradient to 100% MeOH, 80~100 min 100% MeOH; inject volume: 100 μl; inject weight: 5 μg; flow rate: 0.8 ml/min; UV: 220 nm and MS condition: APCI+ mode.

Figure 5:
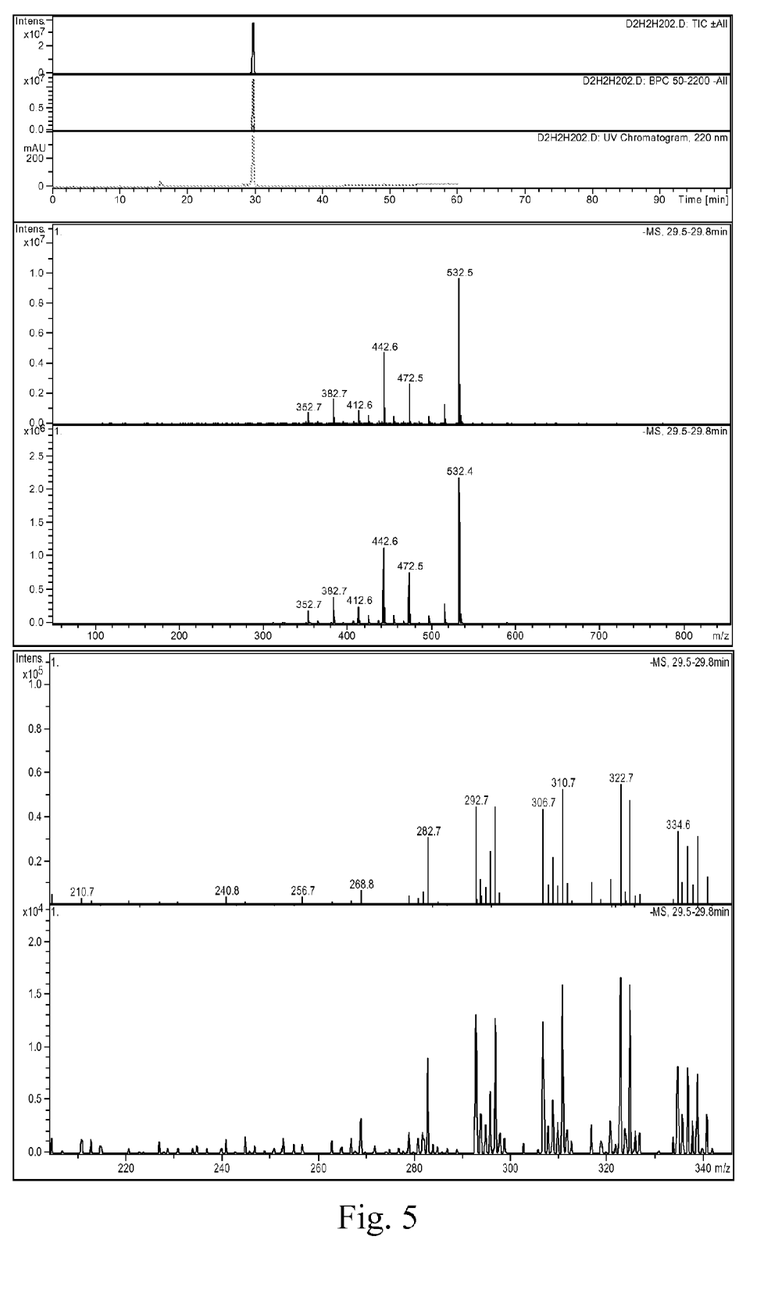
FIG. 5 is another LC-MS chromatography of DCMPbL6, 7D2H2H3H2.

Please refer to FIG. 5, which is another LC-MS chromatography of DCMPbL6,7D2H2H3H2. The analysis conditions for FIG. 5 are: column: Mightysil RP-C18 (4.6×250 mm), 5 μm; mobile phase: 0~80 min MeOH/H₂O=20/80 gradient to 100% MeOH, 80~100 min 100% MeOH; inject volume: 100 μl; inject weight: 5 μg; flow rate: 0.8 ml/min; UV: 220 nm and MS condition: APCI− mode.

Figure 6:
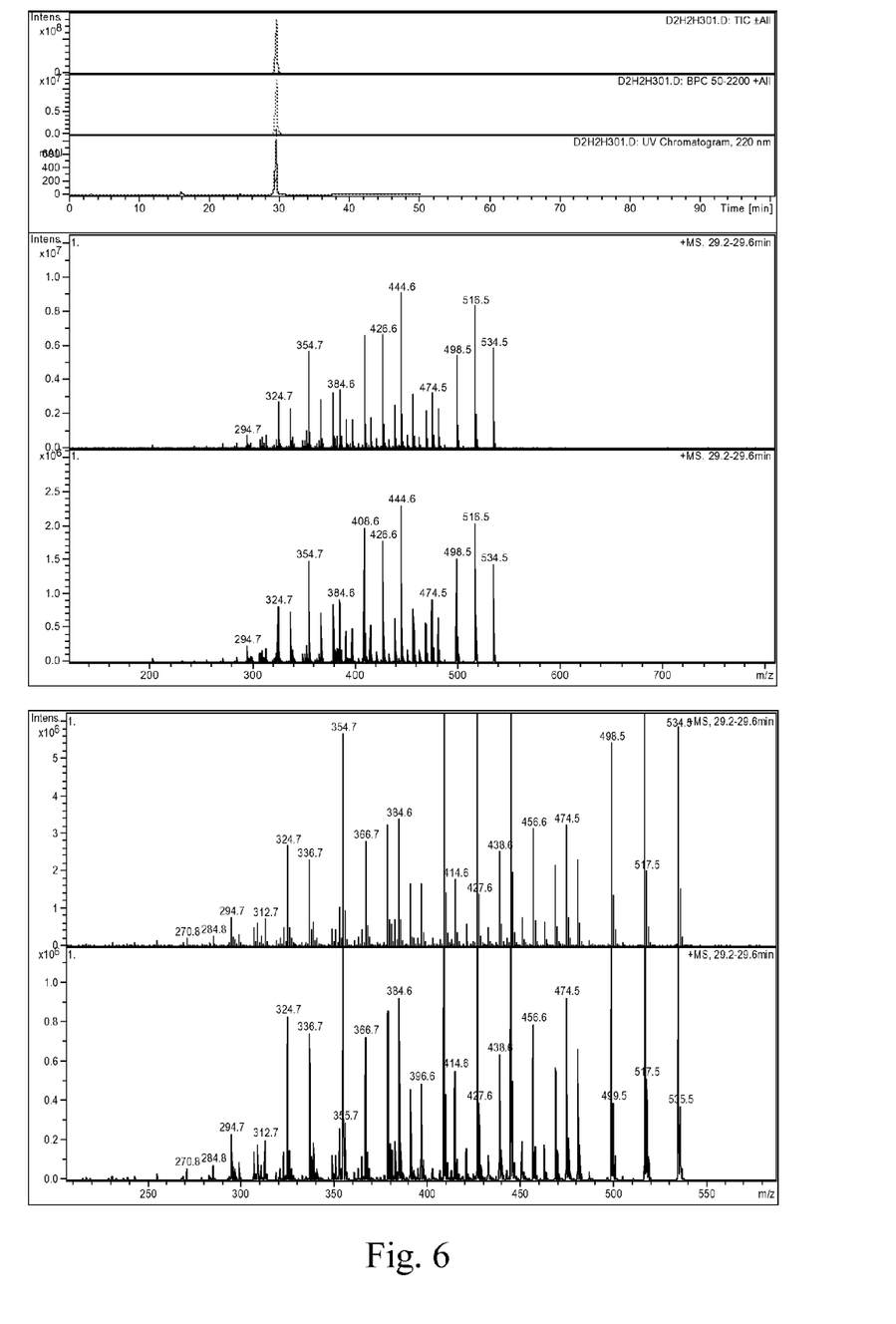
FIG. 6 is the LC-MS chromatography of DCMPbL6, 7D2H2H3H3.

Please refer to FIG. 6, which is the LC-MS chromatography of DCMPbL6,7D2H2H3H3. The analysis conditions for FIG. 6 are: column: Mightysil RP-C18 (4.6×250 mm), 5 μm; mobile phase: 0~80 min MeOH/H₂O=20/80 gradient to 100% MeOH, 80~100 min 100% MeOH; inject volume: 100 μl; inject weight: 5 μg; flow rate: 0.8 ml/min; UV: 220 nm and MS condition: APCI+ mode.

Figure 7:
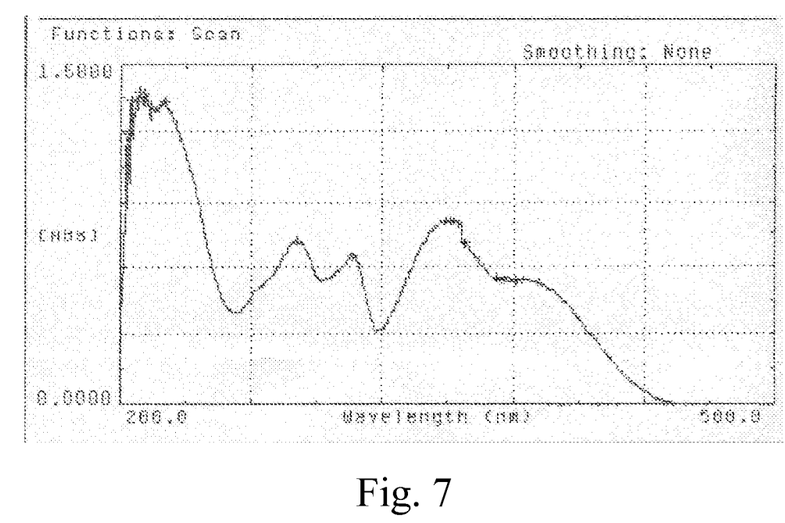
FIG. 7 is the UV spectrum of the methanol solution of DCMPbL6,7D2H2H3H4.

Please refer to FIG. 7, which is the UV spectrum of the methanol solution of DCMPbL6,7D2H2H3H4 (50 μg/ml). As shown in FIG. 7, DCMPbL6,7D2H2H3H4 has characteristic bands: I at λ=334 nm, and band II at λ=275 nm, which leads to the conclusion that the compound belongs to the group of flavonoids.

Based on the above mentioned, it is found that the molecular weight of DCMPbL6,7D2H2H3 is about 534 and it could be one selected from a group consisting of apigenin 6,8-Di-C-α-L-arabinopyranoside, apigenin 6-C-β-D-Xylopyranosyl-8-C-α-L-arabinopyranoside, apigenin 6-C-α-L-Arabinopyranosyl-8-C-β-D-arabinopyranoside and the mixture thereof. The structure of apigenin 6-C-β-D-Xylopyranosyl-8-C-α-L-arabinopyranoside is shown in the following:

M.w. = 534

In addition, the IR analyses of DCMPbL6,7D2H2H3 (not shown herein) shows that the structural features of the DCMPbL6,7D2H2H3 coincide with those of the 6,8-Di-C-glycosides of apigenin.

Furthermore, after being added some agents (AlCl₃, NaOAc, NaOAc+H₃BO₃) thereinto, DCMPbL6, 7D2H2H3H2, DCMPbL6,7D2H2H3H3, DCMPbL6, 7D2H2H3H2 and DCMPbL6,7D2H2H3H4 are proceeded with the UV analyses. The UV results show that the structural features of the DCMPbL6,7D2H2H3H2, DCMPbL6, 7D2H2H3H3, DCMPbL6,7D2H2H3H2 and DCMPbL6, 7D2H2H3H4 coincide with those of the flavonoids (wherein there are hydroxyl groups at C-5 and C-7 positions, but there is no hydroxyl group at C-3 position).

Moreover, after being proceeded with NMR analyses, the H-NMR and C-NMR spectra of DCMPbL6,7D2H2H3, DCMPbL6,7D2H2H3H2, DCMPbL6,7D2H2H3H3 and DCMPbL6,7D2H2H3H4 show that the relevant structural features thereof coincide with those of 6,8-Di-C-glycosides of apigenin. According to the above analyses, DCMPbL6, 7D2H2H3H2 was been characterized as apigenin 6-C-β-D-Xylopyranosyl-8-C-α-L-arabinopyranoside, DCMPbL6, 7D2H2H3H3 was characterized as apigenin 6,8-Di-C-α-L-arabinopyranoside, and DCMPbL6,7D2H2H3H4 was characterized as apigenin 6-C-α-L-Arabinopyranosyl-8-C-β-D-arabinopyranoside.

As above, it is found the substances from DCMPbL6, 7D2H2, i.e. DCMPbL6,7D2H2H3, DCMPbL6, 7D2H2H3H2, DCMPbL6,7D2H2H3H3 and DCMPbL6, 7D2H2H3H4, could be 6,8-Di-C-glycosides of apigenin or the derivatives thereof, and they should have the structure as follows.

wherein R₁ and R₂ are the same or different and are ones selected from a group consisting of α-Arabinose, β-Arabinose and β-Xylose.

However, since the natural C-glycosylflavonoids of C-glycosyl residues include C-β-D-glucopyranosyl, C-β-D-galactopyranosyl, C-β-D-xylopyranosyl, C-β-D-arabinopyranosyl, C-α-L-arabinopyranosyl, C-α-L-rhamnopyranosyl and C-6-deoxy-xylo-hexos-4-ulosyl and the above experiments have shown that DCMPbL6,7D2H2H3, DCMPbL6,7D2H2H3H2, DCMPbL6,7D2H2H3H3 and DCMPbL6,7D2H2H3H4 have the above main structure of C-glycosides, it is believed that when the $R_1$ and $R_2$ are also selected from the above 7 natural C-glycosylflavonoids, 48 relevant compounds will be obtained therefrom. Similarly, if the $R_1$ and $R_2$ are also selected from the unnatural C-glycosyl residues, 482 relevant compounds will be obtained therefrom. Accordingly, if the functional groups at C-4', C-5 and C-7 positions are substituted with other functional groups, the number of the relevant derivatives will be enormous. Table 1 shows the possible natural functional group combinations for $R_1$ and $R_2$.

TABLE 1

The possible natural functional group combinations for $R_1$ and $R_2$.

| Compound | $R_1$ | $R_2$ |
|---|---|---|
| 1* | α-Ara | α-Ara |
| 2* | β-Xyl | α-Ara |
| 3* | α-Ara | β-Xyl |
| 4 | β-Ara | β-Ara |
| 5* | α-Ara | β-Ara |
| 6 | β-Ara | α-Ara |
| 7 | β-Xyl | β-Ara |
| 8 | β-Ara | β-Xyl |
| 9 | c-6-Deoxy-xylo-hexos-4-ulosyl | α-Ara |
| 10 | c-6-Deoxy-xylo-hexos-4-ulosyl | β-Ara |
| 11 | c-6-Deoxy-xylo-hexos-4-ulosyl | β-Xyl |
| 12 | β-Xyl | c-6-Deoxy-xylo-hexos-4-ulosyl |
| 13 | α-Ara | c-6-Deoxy-xylo-hexos-4-ulosyl |
| 14 | β-Ara | c-6-Deoxy-xylo-hexos-4-ulosyl |
| 15 | c-6-Deoxy-xylo-hexos-4-ulosyl | c-6-Deoxy-xylo-hexos-4-ulosyl |
| 16 | α-Ara | β-Glu |
| 17 | α-Ara | β-Gal |
| 18 | β-Ara | β-Glu |
| 19 | β-Ara | β-Gal |
| 20 | β-Glu | α-Ara |
| 21 | β-Gal | α-Ara |
| 22 | β-Glu | β-Ara |
| 23 | β-Gal | β-Ara |
| 24 | β-Xyl | β-Glu |
| 25 | β-Xyl | β-Gal |
| 26 | β-Glu | β-Xyl |
| 27 | β-Gal | β-Xyl |
| 28 | c-6-Deoxy-xylo-hexos-4-ulosyl | β-Glu |
| 29 | c-6-Deoxy-xylo-hexos-4-ulosyl | β-Gal |
| 30 | β-Glu | c-6-Deoxy-xylo-hexos-4-ulosyl |
| 31 | β-Gal | c-6-Deoxy-xylo-hexos-4-ulosyl |
| 32 | α-Ara | α-Rha |
| 33 | β-Ara | α-Rha |
| 34 | α-Rha | α-Ara |
| 35 | α-Rha | β-Ara |
| 36 | β-Xyl | α-Rha |
| 37 | α-Rha | β-Xyl |
| 38 | c-6-Deoxy-xylo-hexos-4-ulosyl | α-Rha |
| 39 | α-Rha | c-6-Deoxy-xylo-hexos-4-ulosyl |
| 40 | β-Glu | β-Glu |
| 41 | β-Glu | β-Gal |
| 42 | β-Gal | β-Glu |
| 43 | β-Gal | β-Gal |
| 44 | β-Glu | α-Rha |
| 45 | α-Rha | β-Glu |
| 46 | β-Gal | α-Rha |
| 47 | α-Rha | β-Gal |
| 48 | α-Rha | α-Rha |

*major products.

Furthermore, the possible unnatural functional group compositions for $R_1$ and $R_2$ are shown in Table 2.

TABLE 2

The possible unnatural functional group compositions for $R_1$ and $R_2$.

| Compound | $R_1$ (or $R_2$) | $R_2$ (or $R_1$) |
|---|---|---|
| 1 | β-Ribose | β-Ribose |
| 2 | β-Ribose | α-Arabinose |
| 3 | β-Ribose | β-Arabinose |
| 4 | β-Ribose | β-Xylose |
| 5 | β-Ribose | β-Lyxose |
| 6 | β-Ribose | β-Allose |
| 7 | β-Ribose | β-Altrose |
| 8 | β-Ribose | β-Mannose |
| 9 | β-Ribose | β-Gulose |
| 10 | β-Ribose | β-Idose |
| 11 | β-Ribose | β-Talose |
| 12 | β-Ribose | β-Tagatose |
| 13 | β-Ribose | β-Fructose |
| 14 | β-Ribose | β-Glucose |
| 15 | β-Ribose | β-Galactose |
| 16 | β-Ribose | α-Rhamnose |
| 17 | β-Ribose | c-6-Deoxy-xylo-hexos-4-ulosyl |
| 18 | α-Arabinose | β-Ribose |
| 19 | α-Arabinose | β-Lyxose |
| 20 | α-Arabinose | β-Allose |
| 21 | α-Arabinose | β-Altrose |
| 22 | α-Arabinose | β-Mannose |
| 23 | α-Arabinose | β-Gulose |
| 24 | α-Arabinose | β-Idose |
| 25 | α-Arabinose | β-Talose |
| 26 | α-Arabinose | β-Tagatose |
| 27 | α-Arabinose | β-Fructose |
| 28 | β-Arabinose | β-Ribose |
| 29 | β-Arabinose | β-Lyxose |
| 30 | β-Arabinose | β-Allose |
| 31 | β-Arabinose | β-Altrose |
| 32 | β-Arabinose | β-Mannose |
| 33 | β-Arabinose | β-Gulose |
| 34 | β-Arabinose | β-Idose |
| 35 | β-Arabinose | β-Talose |
| 36 | β-Arabinose | β-Tagatose |
| 37 | β-Arabinose | β-Fructose |
| 38 | β-Xylose | β-Ribose |
| 39 | β-Xylose | β-Lyxose |
| 40 | β-Xylose | β-Allose |
| 41 | β-Xylose | β-Altrose |
| 42 | β-Xylose | β-Mannose |
| 43 | β-Xylose | β-Gulose |
| 44 | β-Xylose | β-Idose |
| 45 | β-Xylose | β-Talose |
| 46 | β-Xylose | β-Tagatose |
| 47 | β-Xylose | β-Fructose |
| 48 | β-Lyxose | β-Ribose |
| 49 | β-Lyxose | α-Arabinose |
| 50 | β-Lyxose | β-Arabinose |
| 51 | β-Lyxose | β-Xylose |
| 52 | β-Lyxose | β-Lyxose |
| 53 | β-Lyxose | β-Allose |
| 54 | β-Lyxose | β-Altrose |
| 55 | β-Lyxose | β-Mannose |
| 56 | β-Lyxose | β-Gulose |
| 57 | β-Lyxose | β-Idose |
| 58 | β-Lyxose | β-Talose |
| 59 | β-Lyxose | β-Tagatose |
| 60 | β-Lyxose | β-Fructose |
| 61 | β-Lyxose | β-Glucose |
| 62 | β-Lyxose | β-Galactose |
| 63 | β-Lyxose | α-Rhamnose |
| 64 | β-Lyxose | c-6-Deoxy-xylo-hexos-4-ulosyl |
| 65 | β-Allose | β-Ribose |
| 66 | β-Allose | α-Arabinose |
| 67 | β-Allose | β-Arabinose |
| 68 | β-Allose | β-Xylose |
| 69 | β-Allose | β-Lyxose |
| 70 | β-Allose | β-Allose |
| 71 | β-Allose | β-Altrose |
| 72 | β-Allose | β-Mannose |
| 73 | β-Allose | β-Gulose |
| 74 | β-Allose | β-Idose |
| 75 | β-Allose | β-Talose |
| 76 | β-Allose | β-Tagatose |

TABLE 2-continued

The possible unnatural functional group compositions for $R_1$ and $R_2$.

| Compound | $R_1$ (or $R_2$) | $R_2$ (or $R_1$) |
|---|---|---|
| 77 | β-Allose | β-Fructose |
| 78 | β-Allose | β-Glucose |
| 79 | β-Allose | β-Galactose |
| 80 | β-Allose | α-Rhamnose |
| 81 | β-Allose | c-6-Deoxy-xylo-hexos-4-ulosyl |
| 82 | β-Altrose | β-Ribose |
| 83 | β-Altrose | α-Arabinose |
| 84 | β-Altrose | β-Arabinose |
| 85 | β-Altrose | β-Xylose |
| 86 | β-Altrose | β-Lyxose |
| 87 | β-Altrose | β-Allose |
| 88 | β-Altrose | β-Altrose |
| 89 | β-Altrose | β-Mannose |
| 90 | β-Altrose | β-Gulose |
| 91 | β-Altrose | β-Idose |
| 92 | β-Altrose | β-Talose |
| 93 | β-Altrose | β-Tagatose |
| 94 | β-Altrose | β-Fructose |
| 95 | β-Altrose | β-Glucose |
| 96 | β-Altrose | β-Galactose |
| 97 | β-Altrose | α-Rhamnose |
| 98 | β-Altrose | c-6-Deoxy-xylo-hexos-4-ulosyl |
| 99 | β-Mannose | β-Ribose |
| 100 | β-Mannose | α-Arabinose |
| 101 | β-Mannose | β-Arabinose |
| 102 | β-Mannose | β-Xylose |
| 103 | β-Mannose | β-Lyxose |
| 104 | β-Mannose | β-Allose |
| 105 | β-Mannose | β-Altrose |
| 106 | β-Mannose | β-Mannose |
| 107 | β-Mannose | β-Gulose |
| 108 | β-Mannose | β-Idose |
| 109 | β-Mannose | β-Talose |
| 110 | β-Mannose | β-Tagatose |
| 111 | β-Mannose | β-Fructose |
| 112 | β-Mannose | β-Glucose |
| 113 | β-Mannose | β-Galactose |
| 114 | β-Mannose | α-Rhamnose |
| 115 | β-Mannose | c-6-Deoxy-xylo-hexos-4-ulosyl |
| 116 | β-Gulose | β-Ribose |
| 117 | β-Gulose | α-Arabinose |
| 118 | β-Gulose | β-Arabinose |
| 119 | β-Gulose | β-Xylose |
| 120 | β-Gulose | β-Lyxose |
| 121 | β-Gulose | β-Allose |
| 122 | β-Gulose | β-Altrose |
| 123 | β-Gulose | β-Mannose |
| 124 | β-Gulose | β-Gulose |
| 125 | β-Gulose | β-Idose |
| 126 | β-Gulose | β-Talose |
| 127 | β-Gulose | β-Tagatose |
| 128 | β-Gulose | β-Fructose |
| 129 | β-Gulose | β-Glucose |
| 130 | β-Gulose | β-Galactose |
| 131 | β-Gulose | α-Rhamnose |
| 132 | β-Gulose | c-6-Deoxy-xylo-hexos-4-ulosyl |
| 133 | β-Idose | β-Ribose |
| 134 | β-Idose | α-Arabinose |
| 135 | β-Idose | β-Arabinose |
| 136 | β-Idose | β-Xylose |
| 137 | β-Idose | β-Lyxose |
| 138 | β-Idose | β-Allose |
| 139 | β-Idose | β-Altrose |
| 140 | β-Idose | β-Mannose |
| 141 | β-Idose | β-Gulose |
| 142 | β-Idose | β-Idose |
| 143 | β-Idose | β-Talose |
| 144 | β-Idose | β-Tagatose |
| 145 | β-Idose | β-Fructose |
| 146 | β-Idose | β-Glucose |
| 147 | β-Idose | β-Galactose |
| 148 | β-Idose | α-Rhamnose |
| 149 | β-Idose | c-6-Deoxy-xylo-hexos-4-ulosyl |
| 150 | β-Talose | β-Ribose |
| 151 | β-Talose | α-Arabinose |
| 152 | β-Talose | β-Arabinose |
| 153 | β-Talose | β-Xylose |
| 154 | β-Talose | β-Lyxose |
| 155 | β-Talose | β-Allose |
| 156 | β-Talose | β-Altrose |
| 157 | β-Talose | β-Mannose |
| 158 | β-Talose | β-Gulose |
| 159 | β-Talose | β-Idose |
| 160 | β-Talose | β-Talose |
| 161 | β-Talose | β-Tagatose |
| 162 | β-Talose | β-Fructose |
| 163 | β-Talose | β-Glucose |
| 164 | β-Talose | β-Galactose |
| 165 | β-Talose | α-Rhamnose |
| 166 | β-Talose | c-6-Deoxy-xylo-hexos-4-ulosyl |
| 167 | β-Tagatose | β-Ribose |
| 168 | β-Tagatose | α-Arabinose |
| 169 | β-Tagatose | β-Arabinose |
| 170 | β-Tagatose | β-Xylose |
| 171 | β-Tagatose | β-Lyxose |
| 172 | β-Tagatose | β-Allose |
| 173 | β-Tagatose | β-Altrose |
| 174 | β-Tagatose | β-Mannose |
| 175 | β-Tagatose | β-Gulose |
| 176 | β-Tagatose | β-Idose |
| 177 | β-Tagatose | β-Talose |
| 178 | β-Tagatose | β-Tagatose |
| 179 | β-Tagatose | β-Fructose |
| 180 | β-Tagatose | β-Glucose |
| 181 | β-Tagatose | β-Galactose |
| 182 | β-Tagatose | α-Rhamnose |
| 183 | β-Tagatose | c-6-Deoxy-xylo-hexos-4-ulosyl |
| 184 | β-Fructose | β-Ribose |
| 185 | β-Fructose | α-Arabinose |
| 186 | β-Fructose | β-Arabinose |
| 187 | β-Fructose | β-Xylose |
| 188 | β-Fructose | β-Lyxose |
| 189 | β-Fructose | β-Allose |
| 190 | β-Fructose | β-Altrose |
| 191 | β-Fructose | β-Mannose |
| 192 | β-Fructose | β-Gulose |
| 193 | β-Fructose | β-Idose |
| 194 | β-Fructose | β-Talose |
| 195 | β-Fructose | β-Tagatose |
| 196 | β-Fructose | β-Fructose |
| 197 | β-Fructose | β-Glucose |
| 198 | β-Fructose | β-Galactose |
| 199 | β-Fructose | α-Rhamnose |
| 200 | β-Fructose | c-6-Deoxy-xylo-hexos-4-ulosyl |
| 201 | β-Glucose | β-Ribose |
| 202 | β-Glucose | β-Lyxose |
| 203 | β-Glucose | β-Allose |
| 204 | β-Glucose | β-Altrose |
| 205 | β-Glucose | β-Mannose |
| 206 | β-Glucose | β-Gulose |
| 207 | β-Glucose | β-Idose |
| 208 | β-Glucose | β-Talose |
| 209 | β-Glucose | β-Tagatose |
| 210 | β-Glucose | β-Fructose |
| 211 | β-Glucose | c-6-Deoxy-xylo-hexos-4-ulosyl |
| 212 | β-Galactose | β-Ribose |
| 213 | β-Galactose | β-Lyxose |
| 214 | β-Galactose | β-Allose |
| 215 | β-Galactose | β-Altrose |
| 216 | β-Galactose | β-Mannose |
| 217 | β-Galactose | β-Gulose |
| 218 | β-Galactose | β-Idose |
| 219 | β-Galactose | β-Talose |
| 220 | β-Galactose | β-Tagatose |
| 221 | β-Galactose | β-Fructose |
| 222 | α-Rhamnose | β-Ribose |
| 223 | α-Rhamnose | β-Lyxose |
| 224 | α-Rhamnose | β-Allose |
| 225 | α-Rhamnose | β-Altrose |
| 226 | α-Rhamnose | β-Mannose |
| 227 | α-Rhamnose | β-Gulose |
| 228 | α-Rhamnose | β-Idose |

TABLE 2-continued

The possible unnatural functional group compositions for $R_1$ and $R_2$.

| Compound | $R_1$ (or $R_2$) | $R_2$ (or $R_1$) |
|---|---|---|
| 229 | α-Rhamnose | β-Talose |
| 230 | α-Rhamnose | β-Tagatose |
| 231 | α-Rhamnose | β-Fructose |
| 232 | c-6-Deoxy-xylo-hexos-4-ulosyl | β-Ribose |
| 233 | c-6-Deoxy-xylo-hexos-4-ulosyl | β-Lyxose |
| 234 | c-6-Deoxy-xylo-hexos-4-ulosyl | β-Allose |
| 235 | c-6-Deoxy-xylo-hexos-4-ulosyl | β-Altrose |
| 236 | c-6-Deoxy-xylo-hexos-4-ulosyl | β-Mannose |
| 237 | c-6-Deoxy-xylo-hexos-4-ulosyl | β-Gulose |
| 238 | c-6-Deoxy-xylo-hexos-4-ulosyl | β-Idose |
| 239 | c-6-Deoxy-xylo-hexos-4-ulosyl | β-Talose |
| 240 | c-6-Deoxy-xylo-hexos-4-ulosyl | β-Tagatose |
| 241 | c-6-Deoxy-xylo-hexos-4-ulosyl | β-Fructose |

Figure 8:
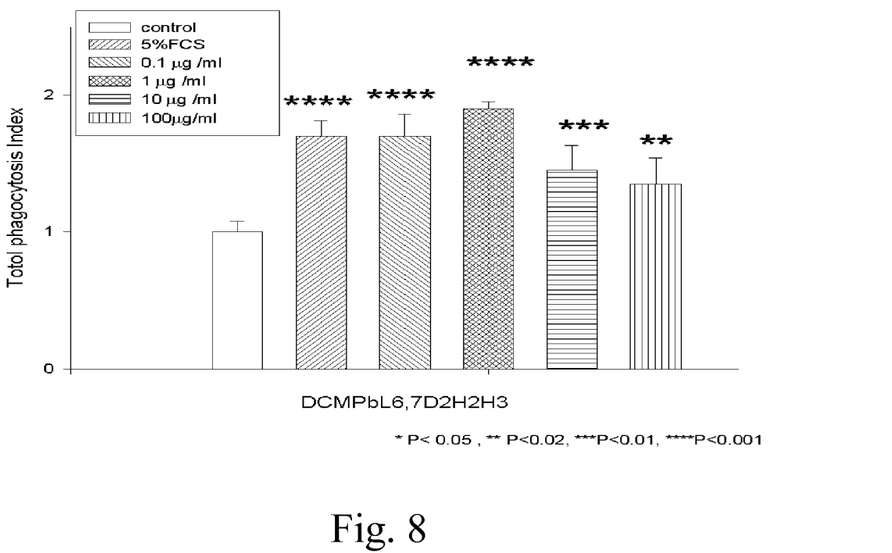
FIG. 8 is the bar chart illustrating the effects of DCMPbL6, 7D2H2H3 on the total phagocytosis of RPE.
Figure 9:
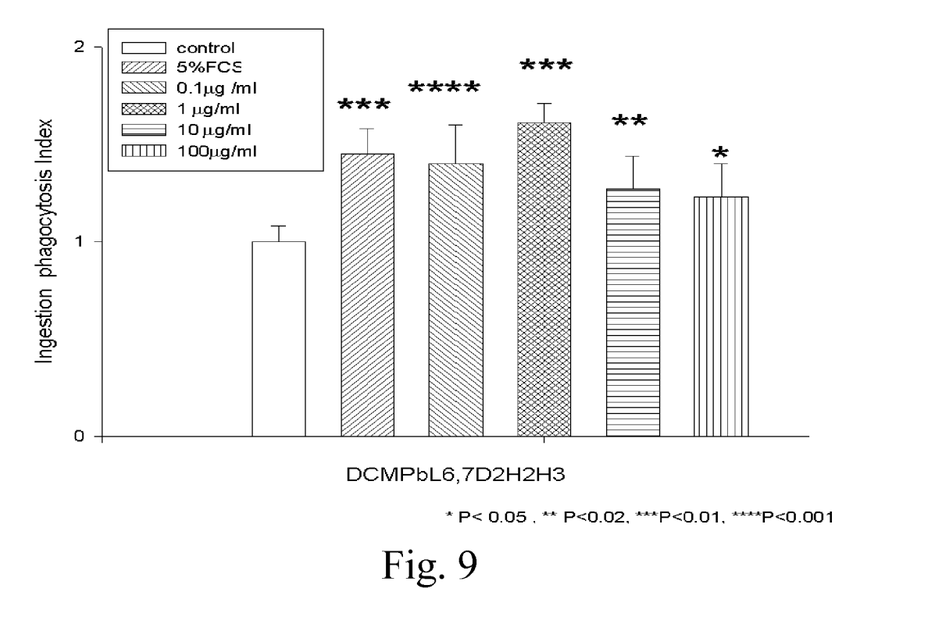
FIG. 9 is the bar chart illustrating the effects of DCMPbL6, 7D2H2H3 on the ingestion phagocytosis of RPE.

Please refer to FIG. 8, which is the bar chart illustrating the effects of DCMPbL6,7D2H2H3 on the total phagocytosis of RPE. As shown in FIG. 8, it's known that various concentrations (0.1, 1, 10, 100 μg/ml) of DCMPbL6,7D2H2H3 can accelerate the phagocytosis of RPE. The relevant experimental contents are simply described as follows. $1\times10^4$ RPE cells are seeded in 96-well microplate per well, containing 5% FCS in DMEM after 48 hrs, and the medium is changed with 2% FCS in DMEM. Then different concentrations of DCMPbL6, 7D2H2H3 are added respectively. After 24 hrs, 50 μl of $2\times10^7$ FITC-ROS/ml is added into each well. Four hours later, the unbounded FITC-ROS is washed out with PBS+2% sucrose. The emission wavelength is 485 nm and the detecting wavelength is 530 nm. The fluorescence intensity is detected by a 1420 Multilable counter (PE) measurement system. The detected fluorescence intensity represents the total phagocytosis. If the fluoro Quench dye is added, the detected fluorescence intensity represents the ingestion phagocytosis. *$P<0.05$, $P<0.02$, *$P<0.01$ and ****$P<0.001$ are obtained by comparing with phagocytosis of RPE treated with 2% FCS. In addition, FIG. 9 is the bar chart illustrating the effects of DCMPbL6,7D2H2H3 on the ingestion phagocytosis of RPE.

Figure 10:
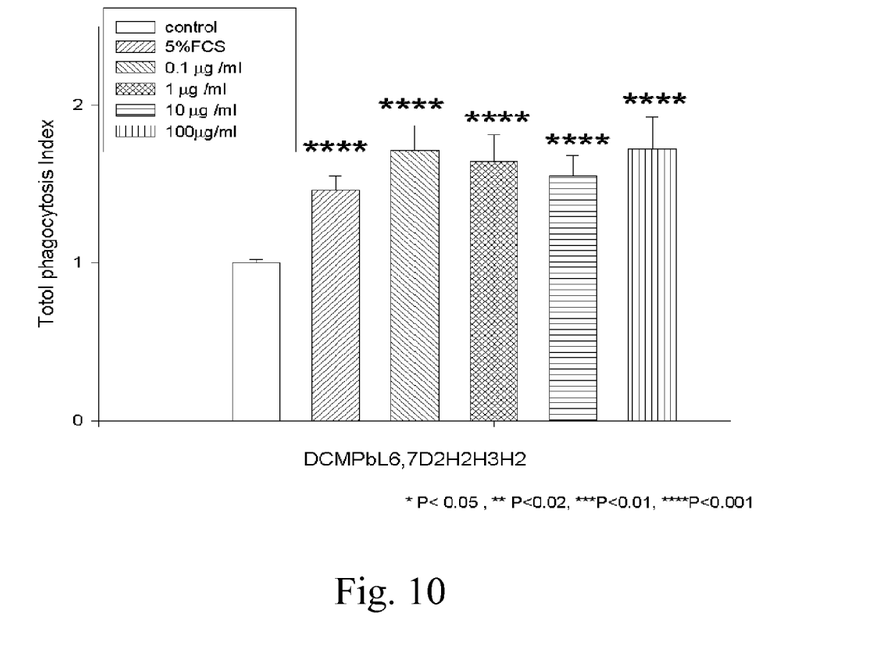
FIG. 10 is the bar chart illustrating the effects of DCMPbL6,7D2H2H3H2 on the total phagocytosis of RPE.
Figure 11:
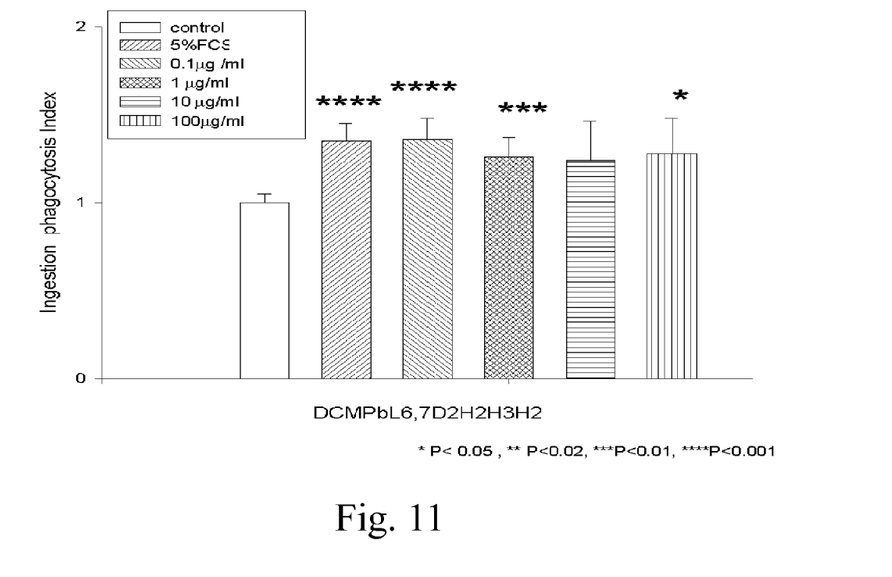
FIG. 11 is the bar chart illustrating the effects of DCMPbL6,7D2H2H3H2 on the ingestion phagocytosis of RPE.

Please refer to FIG. 10, which is the bar chart illustrating the effects of DCMPbL6,7D2H2H3H2 on the total phagocytosis of RPE. As shown in FIG. 10, it's known that various concentrations (0.1, 1, 10, 100 μg/ml) of DCMPbL6, 7D2H2H3H2 can accelerate the phagocytosis of RPE. The relevant experimental contents are simply described as follows. $1\times10^4$ RPE cells are seeded in 96-well microplate per well, containing 5% FCS in DMEM after 48 hrs, and the medium is changed with 2% FCS in DMEM. Then different concentrations of DCMPbL6,7D2H2H3H2 are added respectively. After 24 hrs, 50 μl of $2\times10^7$ FITC-ROS/ml is added into each well. Four hours later, the unbounded FITC-ROS is washed out with PBS+2% sucrose. The emission wavelength is 485 nm and the detecting wavelength is 530 nm. The fluorescence intensity is detected by a 1420 Multilable counter (PE) measurement system. The detected fluorescence intensity represents the total phagocytosis. If the fluoro Quench dye is added, the detected fluorescence intensity represents the ingestion phagocytosis. *$P<0.05$, $P<0.02$, *$P<0.01$ and ****$P<0.001$ are obtained by comparing with phagocytosis of RPE treated with 2% FCS. In addition, FIG. 11 is the bar chart illustrating the effects of DCMPbL6, 7D2H2H3H2 on the ingestion phagocytosis of RPE.

Figure 12:
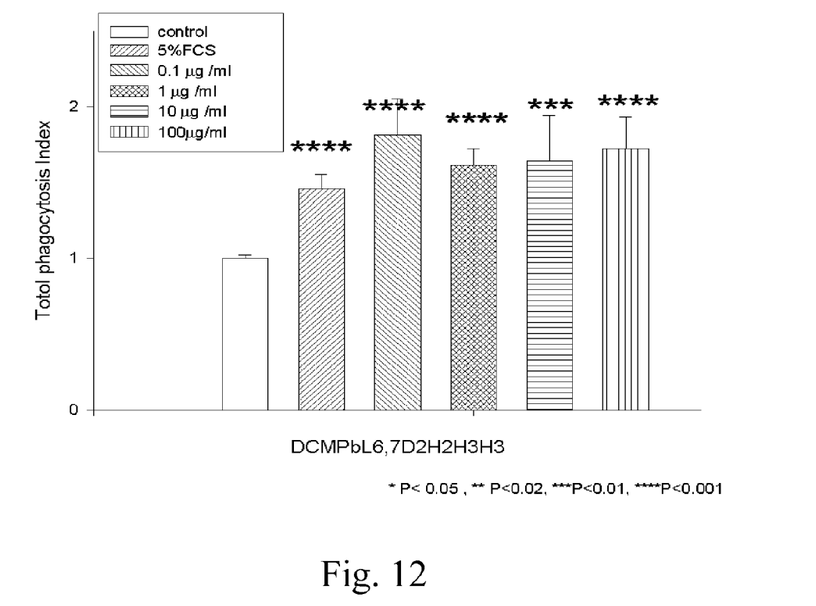
FIG. 12 is the bar chart illustrating the effects of DCMPbL6,7D2H2H3H3 on the total phagocytosis of RPE.
Figure 13:
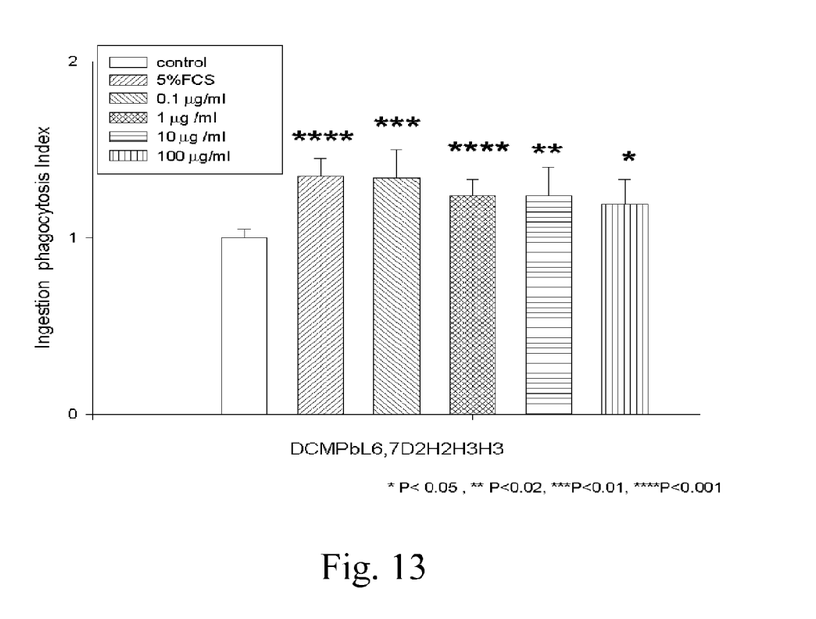
FIG. 13 is the bar chart illustrating the effects of DCMPbL6,7D2H2H3H3 on the ingestion phagocytosis of RPE.

Please refer to FIG. 12, which is the bar chart illustrating the effects of DCMPbL6,7D2H2H3H3 on the total phagocytosis of RPE. As shown in FIG. 12, it's known that various concentrations (0.1, 1, 10, 100 μg/ml) of DCMPbL6, 7D2H2H3H3 can accelerate the phagocytosis of RPE. The relevant experimental contents are simply described as follows. $1\times10^4$ RPE cells are seeded in 96-well microplate per well, containing 5% FCS in DMEM after 48 hrs, and the medium is changed with 2% FCS in DMEM. Then different concentrations of DCMPbL6,7D2H2H3H3 are added respectively. After 24 hrs, 50 μl of $2\times10^7$ FITC-ROS/ml is added into each well. Four hours later, the unbounded FITC-ROS is washed out with PBS+2% sucrose. The emission wavelength is 485 nm and the detecting wavelength is 530 nm. The fluorescence intensity is detected by a 1420 Multilable counter (PE) measurement system. The detected fluorescence intensity represents the total phagocytosis. If the fluoro Quench dye is added, the detected fluorescence intensity represents the ingestion phagocytosis. *$P<0.05$, $P<0.02$, *$P<0.01$ and ****$P<0.001$ are obtained by comparing with phagocytosis of RPE treated with 2% FCS. In addition, FIG. 13 is the bar chart illustrating the effects of DCMPbL6, 7D2H2H3H3 on the ingestion phagocytosis of RPE.

Figure 14:
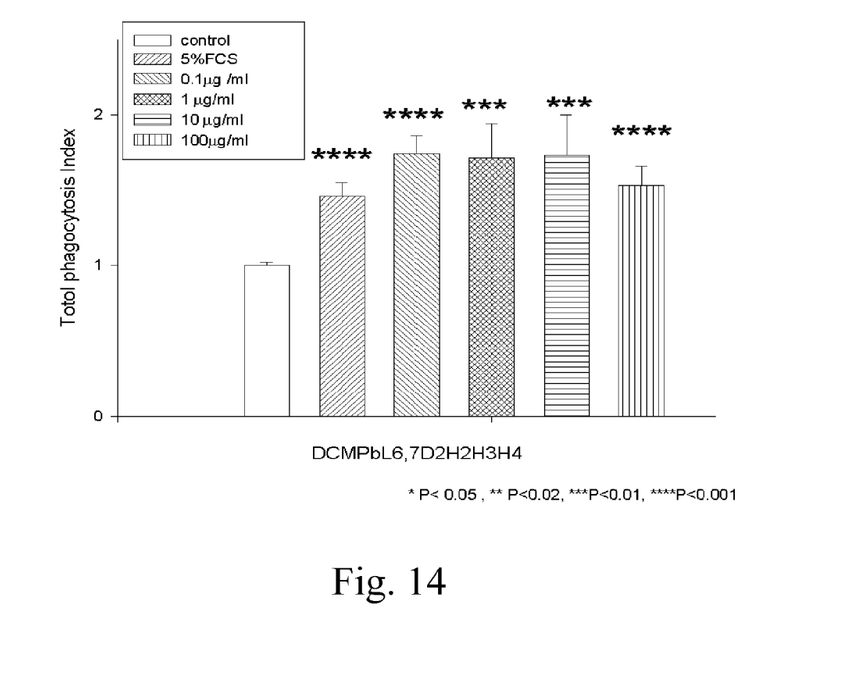
FIG. 14 is the bar chart illustrating the effects of DCMPbL6,7D2H2H3H4 on the total phagocytosis of RPE.
Figure 15:
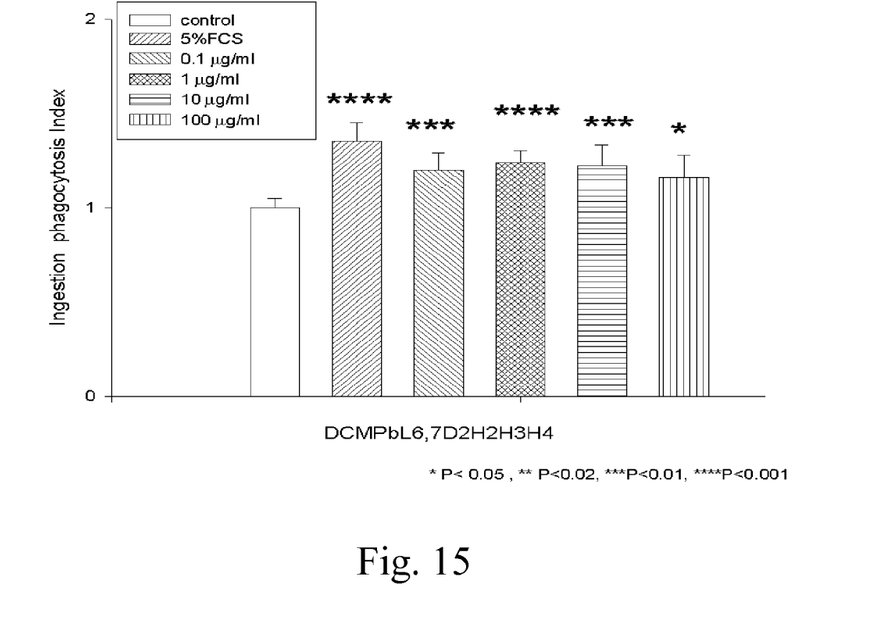
FIG. 15 is the bar chart illustrating the effects of DCMPbL6,7D2H2H3H4 on the ingestion phagocytosis of RPE.

Please refer to FIG. 14, which is the bar chart illustrating the effects of DCMPbL6,7D2H2H3H4 on the total phagocytosis of RPE. As shown in FIG. 14, it's known that various concentrations (0.1, 1, 10, 100 μg/ml) of DCMPbL6, 7D2H2H3H4 can accelerate the phagocytosis of RPE. The relevant experimental contents are simply described as follows. $1\times10^4$ RPE cells are seeded in 96-well microplate per well, containing 5% FCS in DMEM after 48 hrs, and the medium is changed with 2% FCS in DMEM. Then different concentrations of DCMPbL6,7D2H2H3H4 are added respectively. After 24 hrs, 50 μl of $2\times10^7$ FITC-ROS/ml is added into each well. Four hours later, the unbounded FITC-ROS is washed out with PBS+2% sucrose. The emission wavelength is 485 nm and the detecting wavelength is 530 nm. The fluorescence intensity is detected by a 1420 Multilable counter (PE) measurement system. The detected fluorescence intensity represents the total phagocytosis. If the fluoro Quench dye is added, the detected fluorescence intensity represents the ingestion phagocytosis. *$P<0.05$, $P<0.02$, *$P<0.01$ and ****$P<0.001$ are obtained by comparing with phagocytosis of RPE treated with 2% FCS. In addition, FIG. 15 is the bar chart illustrating the effects of DCMPbL6, 7D2H2H3H4 on the ingestion phagocytosis of RPE.

Based on FIGS. 2-7, it seems that DCMPbL6,7D2H2H3, DCMPbL6,7D2H2H3H2, DCMPbL6,7D2H2H3H3 and DCMPbL6,7D2H2H3H4, could be 6,8-Di-C-glycosides of apigenin or the derivatives thereof, and they should have the structure as follows.

wherein $R_1$ and $R_2$ are the same or different and are ones selected from Table 1 and Table 2.

Furthermore, based on FIGS. 8-15, it is known that DCMPbL6,7D2H2H3, DCMPbL6,7D2H2H3H2, DCMPbL6,7D2H2H3H3 and DCMPbL6,7D2H2H3H4 could accelerate the phagocytosis of RPE. As above mentioned, it is realized that the substance with the mentioned structure would accelerate the phagocytosis of RPE.

Furthermore, based on the prior references, it is realized that a composition including the substance capable of accelerating the phagocytosis of RPE would have effects on at least one selected from the groups consisting of retinal neuropathy, RPE degeneration, choroidal neovascularization, proliferative retinopathy, age-related macular degeneration, photoreceptor degeneration, and diabetes vascular complication.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A method for treating a retinal pigment epithelium (RPE) related disorder comprising administering to a human in need thereof a composition comprising a physiologically acceptable carrier and a compound having a structure of formula 1:

Formula 1 at an amount effective in enhancing the function of RPE, wherein each of $R_1$ and $R_2$ is selected from the group consisting of C-6-Deoxy-xylo-hexos-4-ulosyl, α-Arabinose, β-Ribose, β-Xylose, β-Lyxose, β-Allose, β-Altrose, β-Mannose, β-Gulose, β-Idose, β-Talose, β-Tagatose, β-Fructose, β-Galactose, β-Glucose, β-Arabinose, and α-Rhamnose, and $R_1$ and $R_2$ are attached to C-6 and C-8 positions of formula 1, respectively, as C-glycosides, and wherein the RPE related disorder is selected from the group consisting of RPE degeneration, age-related macular degeneration, photoreceptor degeneration, choroidal neovascularization, and proliferative retinopathy.

2. The method of claim 1, wherein $R_1$ and $R_2$ are selected from the group consisting of α-Arabinose, β-Arabinose, and β-Xylose, and $R_1$ and $R_2$ are attached to C-6 and C-8 positions of formula 1, respectively, as C-glycosides.

3. The method of claim 1, wherein $R_1$ and $R_2$ are the same or different and are selected from the group consisting of C-β-D-glucopyranosyl, C-β-D-galactopyranosyl, C-β-D-xylopyranosyl, C-β-D-arabinopyranosyl, C-α-L-arabinopyranosyl, C-α-L-rhamnopyranosyl and C-6-deoxy-xylo-hexos-4-ulosyl.

4. The method of claim 1, wherein the compound is selected from the group consisting of
apigenin 6,8-Di-C-α-L-arabinopyranoside,
apigenin 6-C-β-D-Xylopyranosyl-8-C-α-L-arabinopyranoside, and
apigenin 6-C-α-L-Arabinopyranosyl-8-C-β-D-arabinopyranoside.

5. The method of claim 1, wherein the compound is isolated from *Herba Dendrobii*.

6. The method of claim 1, wherein the compound is effective in enhancing the phagocytic ability of RPE.

7. The method of claim 6, wherein $R_1$ and $R_2$ are selected from the group consisting of α-Arabinose, β-Arabinose, and β-Xylose, and $R_1$ and $R_2$ are attached to C-6 and C-8 positions of formula 1, respectively, as C-glycosides.

8. The method of claim 6, wherein $R_1$ and $R_2$ are the same or different and are selected from the group consisting of C-β-D-glucopyranosyl, C-β-D-galactopyranosyl, C-β-D-xylopyranosyl, C-β-D-arabinopyranosyl, C-α-L-arabinopyranosyl, C-α-L-rhamnopyranosyl and C-6-deoxy-xylo-hexos-4-ulosyl.

9. The method of claim 6, wherein the compound is selected from the group consisting of
apigenin 6,8-Di-C-α-L-arabinopyranoside,
apigenin 6-C-β-D-Xylopyranosyl-8-C-α-L-arabinopyranoside, and
apigenin 6-C-α-L-Arabinopyranosyl-8-C-β-D-arabinopyranoside.

10. The method of claim 6, wherein the compound is isolated from *Herba Dendrobii*.

11. The method of claim 6, wherein the phagocytosis of RPE is enhanced.

* * * * *